United States Patent [19]
Berg et al.

[11] Patent Number: 5,951,586
[45] Date of Patent: Sep. 14, 1999

[54] INTRALUMINAL STENT

[75] Inventors: Eric P. Berg, Plymouth; Rodney G. Wolff, Minetonka Beach; Elaine P. Lindell, Blaine; Paul V. Trescony, Champlin; Matthew A. Bergan, Brooklyn Park; Robert S. Schwartz, Rochester, all of Minn.

[73] Assignee: Medtronic, Inc., Minneapolis, Minn.

[21] Appl. No.: 08/853,204

[22] Filed: May 9, 1997

Related U.S. Application Data

[60] Provisional application No. 60/018,361, May 15, 1996.

[51] Int. Cl.⁶ .................................................. A61M 29/00
[52] U.S. Cl. ............................................... 606/198; 623/1
[58] Field of Search .................................. 623/1, 11, 12; 604/96; 606/191, 192, 193, 194, 195, 198

[56] References Cited

U.S. PATENT DOCUMENTS

| | | |
|---|---|---|
| 4,459,252 | 7/1984 | MacGregor . |
| 4,632,842 | 12/1986 | Karwoski et al. . |
| 4,652,263 | 3/1987 | Herweck et al. . |
| 4,661,530 | 4/1987 | Gogolewski et al. . |
| 4,718,907 | 1/1988 | Karwoski et al. . |
| 4,776,337 | 10/1988 | Palmaz . |
| 4,834,746 | 5/1989 | Kira . |
| 4,979,959 | 12/1990 | Guire . |
| 5,013,306 | 5/1991 | Solomon et al. . |
| 5,019,096 | 5/1991 | Fox, Jr. et al. . |
| 5,037,377 | 8/1991 | Alonso . |
| 5,122,110 | 6/1992 | McNally et al. . |
| 5,132,066 | 7/1992 | Charlsesworth et al. . |
| 5,163,952 | 11/1992 | Froix . |
| 5,163,958 | 11/1992 | Pinchuk . |
| 5,171,217 | 12/1992 | March et al. . |
| 5,222,971 | 6/1993 | Willard et al. . |
| 5,246,451 | 9/1993 | Trescony et al. . |
| 5,258,020 | 11/1993 | Froix . |
| 5,282,472 | 2/1994 | Companion et al. . |
| 5,292,321 | 3/1994 | Lee . |
| 5,304,121 | 4/1994 | Sahatjian . |
| 5,306,286 | 4/1994 | Stack et al. . |
| 5,314,688 | 5/1994 | Kauffman et al. . |
| 5,336,518 | 8/1994 | Narayanan et al. . |
| 5,342,621 | 8/1994 | Eury . |
| 5,356,433 | 10/1994 | Rowland et al. . |
| 5,380,299 | 1/1995 | Fearnot et al. . |
| 5,383,928 | 1/1995 | Scott et al. . |
| 5,419,760 | 5/1995 | Narcisco, Jr. . |

(List continued on next page.)

FOREIGN PATENT DOCUMENTS

| | | |
|---|---|---|
| 0130401 A2 | 1/1985 | European Pat. Off. .......... A61F 2/00 |
| 0143638 A2 | 6/1985 | European Pat. Off. ........ B29C 47/00 |
| 0157178 A1 | 10/1985 | European Pat. Off. .......... A61F 2/06 |
| 0271216 A2 | 6/1988 | European Pat. Off. .......... A61F 2/06 |
| 0332371 A1 | 9/1989 | European Pat. Off. ........ B29D 23/22 |
| 06596389 A1 | 6/1995 | European Pat. Off. .......... A61F 2/06 |
| 2092894 | 8/1982 | United Kingdom .............. A61F 1/00 |

*Primary Examiner*—Michael Buiz
*Assistant Examiner*—Vy Q. Bui
*Attorney, Agent, or Firm*—Daniel W. Latham; Harold R. Patton

[57] ABSTRACT

Intraluminal stents and methods of manufacturing intraluminal stents are disclosed in which the stents have a plurality of recesses in the body of the stent, at least some of the recesses preferably providing a plurality of passageways between the inner and outer surfaces of the stent. The preferred stents are constructed of films on support structures having spaced apart elements, with the films having a thickness of between about 25 micrometers and about 400 micrometers. The stent can also be treated with an anti-thrombotic or a thrombolytic substance and, in some cases, the stents can incorporate therapeutic agents for delivery. The methods of manufacturing stents include forming the films using a solid particulate material that can be substantially removed after the film is formed, thereby forming the recesses and corresponding passageways described above. In preferred methods, the solid particulate material is soluble in a solvent in which the film is substantially insolvent.

24 Claims, 9 Drawing Sheets

U.S. PATENT DOCUMENTS

| | | |
|---|---|---|
| 5,439,446 | 8/1995 | Barry . |
| 5,443,458 | 8/1995 | Eury . |
| 5,449,372 | 9/1995 | Schmaltz et al. . |
| 5,449,382 | 9/1995 | Dayton . |
| 5,464,650 | 11/1995 | Berg et al. . |
| 5,474,563 | 12/1995 | Myler et al. . |
| 5,499,994 | 3/1996 | Tihon et al. . |
| 5,500,013 | 3/1996 | Buscemi et al. . |
| 5,554,182 | 9/1996 | Dinh et al. . |
| 5,571,166 | 11/1996 | Dinh et al. . |
| 5,591,224 | 1/1997 | Schwartz et al. . |
| 5,591,227 | 1/1997 | Dinh et al. . |
| 5,599,352 | 2/1997 | Dinh et al. . |
| 5,607,464 | 3/1997 | Trescony et al. . |
| 5,607,467 | 3/1997 | Froix . |
| 5,609,629 | 3/1997 | Fearnot et al. . |
| 5,624,411 | 4/1997 | Tuch . |
| 5,624,674 | 4/1997 | Seare, Jr. . |
| 5,637,113 | 6/1997 | Tartaglia et al. . |
| 5,735,897 | 4/1998 | Buirge ............ 623/12 |

INTRALUMINAL STENT

RELATED APPLICATIONS

This application is a regular utility application filed claiming priority from U.S. provisional patent application Ser. No. 60/018,361 filed May 15, 1996, which is hereby incorporated by reference in its entirety.

BACKGROUND OF THE INVENTION

This invention relates to a method for lessening restenosis of body lumens and to intraluminal stents having antithrombosis and anti-restenosis properties.

Restenosis is the closure of a peripheral or coronary artery following trauma to the artery caused by efforts to open an occluded portion of the artery, such as, for example, by dilation, ablation, atherectomy or laser treatment of the artery. For these angioplasty procedures, restenosis occurs at a rate of about 20–50% depending on the vessel location, lesion length and a number of other variables. Restenosis is believed to be a natural healing reaction to the injury of the arterial wall that is caused by angioplasty procedures. The healing reaction begins with the clotting of blood at the site of the injury. The final result of the complex steps of the healing process is intimal hyperplasia, the migration and proliferation of medial smooth muscle cells, until the artery is again stenotic or occluded.

In an attempt to prevent restenosis, metallic intravascular stents have been permanently implanted in coronary or peripheral vessels. The stent is typically inserted by catheter into a vascular lumen and expanded into contact with the diseased portion of the arterial wall, thereby providing internal support for the lumen. However, it has been found that restenosis can still occur with such stents in place. Also, the stent itself can cause undesirable local thrombosis. To address the problem of thrombosis, persons receiving stents also receive extensive systemic treatment with anticoagulant and antiplatelet drugs.

To address the restenosis problem, it has been proposed to provide stents which are seeded with endothelial cells (Dichek, D. A. et al Seeding of Intravascular Stents With Genetically Engineered Endothelial Cells; Circulation 1989; 80: 1347– 1353). In that experiment, sheep endothelial cells that had undergone retrovirus-mediated gene transfer for either bacterial beta-galactosidase or human tissue-type plasmogen activator were seeded onto stainless steel stents and grown until the stents were covered. The cells were therefore able to be delivered to the vascular wall where they could provide therapeutic proteins. Other methods of providing therapeutic substances to the vascular wall by means of stents have also been proposed such as in international patent application WO 91/12779 "Intraluminal Drug Eluting Prosthesis" and international patent application WO 90/13332 "Stent With Sustained Drug Delivery ". In those applications, it is suggested that antiplatelet agents, anticoagulant agents, antimicrobial agents, antimetabolic agents and other drugs could be supplied in stents to reduce the incidence of restenosis.

Stents employing anticoagulant substances such as heparin and thrombolitic agents have been proposed in many patents such as U.S. Pat. Nos. 5,419,760; 5,342,621; 5,380,299; 5,429,634; 5,304,121; 5,383,928; 5,443,458; 5,336,518; 5,356,433; 5,464,650; 5,449,382; 5,292,321; 5,439,446; 5,500,013; 5,222,971; and 5,449,372. In particular, it has been recognized that in order to obtain truly antithrombogenic surfaces, proper immobilization of the biomolecules is key. Larm presented (in U.S. Pat. No. 4,613,665) a method to activate heparin via a controlled nitrous acid degradation step, resulting in degraded heparin molecules of which a part contains a free terminal aldehyde group. Heparin in this form can be covalently bound to an aminated surface in a reductive amination process. Although the molecule is degraded and as a result shows less catalytic activity in solution, the end point attachment of this type of heparin to a surface results in true anti-thromogenicity due to the proper presentation of the biomolecule to the surface. In this fashion, the molecule is freely interacting with AT-III and the coagulation enzymes, preventing the generation of thrombi and microemboli.

Besides the coupling of heparin via its natural functional groups or through a terminal aldehyde group, coupling of heparin via aldehyde groups randomly introduced into the chain by means of periodate oxidation has also been described. Solomon et al (in U.S. Pat. Nos. 4,600,652 and 4,642,242) and Hu et al (in U.S. Pat. Nos. 4,720,512; 4,786,556; 5,032,666 and 5,077,372) coupled heparin after periodate oxidation to an aminated polyurethane obtaining a material with high loading of stably bound heparin with the inventors claiming excellent antithrombogenicity for the material.

Also proposed are stents which employ perforations or pores through which tissue ingrowth can occur such as U.S. Pat. Nos. 4,776,337; 5,163,598; 5,163,952; 5,258,020; and 5,306,286. U.S. Pat. No. 5,258,020 discloses a stent made entirely of a polymer that exhibits an elastic memory that facilitates expansion of the stent within a blood vessel.

SUMMARY OF THE INVENTION

The present invention provides methods of manufacturing stents having a plurality of recesses in the body of the stent, at least some of the recesses preferably providing a plurality of passageways between the inner and outer surfaces of the stent. While we do not wish to be bound by theory, it is believed that the recesses provide a locus for deposition of substances in the blood stream, such as fibrin, which are part of the body's natural healing response and are therefore recognized by the immune system as "friendly" rather than "foreign" bodies. Testing of this concept has revealed that a very thin neointima has formed on the stent at 28 days following implantation rather than the thicker neointima typical of implanted stents.

The recesses may be smaller than one micrometer in diameter or as large as 1000 micrometers in diameter, more preferably about one micrometer to about 100 micrometers, and even more preferably about 25 micrometers to about 60 micrometers. It is preferred that the passageways formed by the recesses have diameters of about 5 micrometers to about 100 micrometers to facilitate cell migration through the passageways. Our testing of this concept, as well as the literature, has revealed that cells can migrate easily into passageways formed in such stents.

The stent can also be treated with an antithrombotic or a thrombolytic substance that is capable of reducing the incidence of restenosis at the site of a vascular injury. If so treated, it is preferred that the antithrombotic or thrombolytic substances do not block the passageways formed in the stent. The presence of antithrombogenic or thrombolytic agents on or in the land portions of the blood-contacting surface provide protection against acute thrombosis that is otherwise likely to occur with an irregular surface having such recesses.

In one aspect, methods of manufacturing stents according to the present invention include steps of coating at least a portion of a mandrel with particulate material, the particulate material being soluble in a first solvent; coating at least a portion of the mandrel with a film-forming material, wherein the film-forming material is insoluble in the first solvent; curing the film-forming material on the mandrel to form the body of the stent; and dissolving the particulate material with the first solvent, wherein a plurality of recesses are formed in the body.

The methods according to the present invention may also include forming the plurality of recesses in both the inner and outer surfaces of the body. If so formed, it is preferred that at least some of the plurality of recesses in the inner surface open into at least some of the plurality of recesses in the outer surface to form the plurality of passageways between the inner and outer surfaces of the body. It may also be desirable to coat the film-forming material on the mandrel with the particulate material before the step of curing the film-forming material.

The method according to the present invention may also include a support structure including spaced-apart elements, typically wires. It is preferred that wire be wrapped around the mandrel before coating the mandrel with the film-forming material. It is even more preferred that the wire be wrapped around the mandrel before the step of coating the mandrel with the first particulate material.

The film-forming material may include metallic, polymeric, or metallic and polymeric materials. Preferably, the film-forming material is a polymer solution.

At some point during the manufacturing process, stents according to the present invention include a body having a generally cylindrical shape, the body having an outer surface and an inner surface; and particulate material embedded into the body, the particulate material being soluble in a first solvent.

It is preferred that the particulate material is embedded proximate the inner and outer surfaces of the body. The body of the stent may also include a supporting structure having spaced-apart elements, such as metallic or polymeric wires.

It is also preferred that the body of the stent comprise a film, wherein the particulate material is embedded in the film. The film can be formed of polymers, metals, and combinations thereof.

Stents according to the present invention can be made in virtually any configuration and can be delivered conventionally by catheter to the site of the luminal closure or restriction. A method for making such a stent and a method for treating restenosis with the stent is also disclosed.

DETAILED DESCRIPTION OF THE INVENTION

Figure 1:
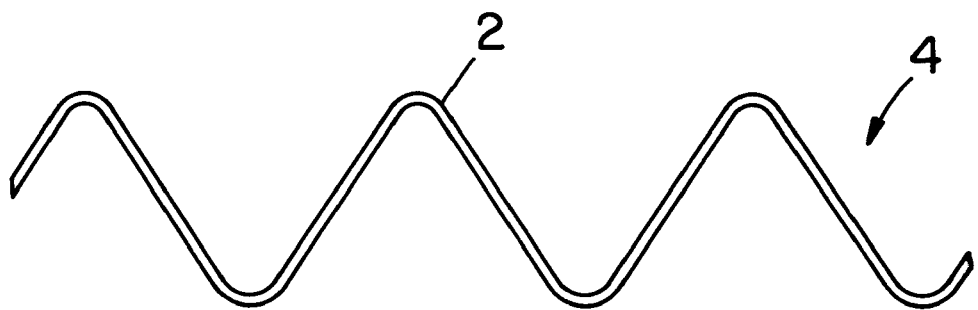
FIG. 1 is a plan view of a zig-zag wire for use in a stent according to the present invention.

The term "stent" herein means a medical implant in the form of a hollow cylinder which when implanted into contact with a site in the wall of a lumen to be treated, will provide support for the body lumen. This can include especially devices delivered percutaneously to treat coronary artery occlusions and to seal dissections or aneurysms of splenic, carotid, iliac and popliteal vessels.

Preferably, the stent of the present invention is adapted for use in blood vessels such that the stent has an outer, lumen-contacting surface, and an inner, blood-contacting surface. The stent can also have underlying polymeric or metallic structural elements onto which a film is applied. For example, a deformable metal wire stent such as that disclosed in U.S. Pat. No. 4,886,062 issued to Wiktor, which is incorporated by reference herein in its entirety, has spaced-apart metal elements which would be suitable for a stent according to the present invention.

The intraluminal stent according to the present invention includes complete 360 degree luminal coverage with a plurality of recesses on the blood contacting surface and the outer luminal surface. The blood contacting surface includes a plurality of lands separating the recesses formed therein. The lands can be treated with an antithrombotic or a thrombolitic substance to provide protection against acute thrombosis that is otherwise likely to occur with an irregular surface having such recesses.

The recesses in both the outer luminal surface and the inner blood-contacting surface may be as small as one micrometer in diameter or as large as 1000 micrometers in diameter, preferably about 1 micrometer to about 100 micrometers, and even more preferably about 25 micrometers to about 60 micrometers. The recesses can be formed as pores in a polymeric film or can also be produced by layering small fibers of metals, polymers, or metals and polymers and pressing them together to form an irregular surface.

Preferably, the recesses communicate with the luminal portion of the stent by means of communicating passageways between the recesses on the blood-contacting surface and the lumen-contacting surface of the stent. In other words, at least some of the recesses formed in the luminal surface preferably open into the recesses formed in the opposing blood-contacting surface, whereby a plurality of passageways are formed through the body of the stent. The passageways are preferably large enough to allow cellular ingrowth through the passageways. Passageways having a diameter in the range of about 5 microns to about 100 microns have been found to readily permit cellular migration and growth.

It is also preferred that the stent be made with a structure which supports its blood-contacting and lumen-contacting surfaces. Spaced-apart metal elements, such as those discussed above, can be coupled to a film having the properties indicated above. Preferably, the spaced-apart metal elements are incorporated into the material forming the recesses so that the metal elements are at least partially confined or encapsulated within the film. More preferably, the spaced-apart metal elements are completely encapsulated within the film.

The thickness of the films used in connection with the present invention can vary. The films are not intended to serve as structural support mechanisms for the tissue between spaced-apart elements of the stents. Rather, the films are supplied primarily to provide a framework for tissue growth and, optionally, as a mechanism for carrying and/or delivering, e.g., antithrombotic or thrombolytic substances or other therapeutic agents. A preferred range for the thickness of the films is about 25 micrometers to about 400 micrometers.

The thickness of the film can be based on a variety of factors. In general, however, it is desirable for the film to be thick enough to at least partially encapsulate the spaced-apart elements supporting the film, more preferably the film is thick enough to completely encapsulate the spaced-apart elements used to support the film.

The porous films used in connection with the present invention are also preferably provided with a grafted antithrombogenic or thrombolytic surface which does not obstruct the recesses and passageways formed in the films. It may be further preferred to provide the antithrombogenic or thrombolytic surface only on the lands of the film, i.e., those portions of the film that are located between the recesses and/or passageways formed in the films.

Intraluminal stents including a thin film having recesses and passageways as discussed above, in combination with antithrombogenic or thrombolytic substances which do not block the recesses and/or passageways can provide significant advantages. Although we do not wish to be bound by any particular theory, it is considered that such a stent provides a locus for deposition of substances in the blood stream, such as fibrin, which are part of the body's natural healing response and are therefore recognized by the immune system as "friendly" rather than "foreign" bodies is maintained. Because the film is relatively thin and at least the exposed surfaces are provided with antithrombogenic or thrombolytic substances, the responses generally considered to cause the thicker neointima typical of implanted stents may be avoided when implanting stents manufactured according to the present invention. As indicated above, tests performed on representative stents have revealed that a limited neointima has formed on the stent at 28 days following implantation.

The methods of manufacturing stents incorporating films in accordance with the present invention include forming the films using a solid particulate material that can be substantially removed after the film is formed, thereby forming the recesses and corresponding passageways described above. By using a solid particulate material during film formation, the size of the recesses and corresponding passageways can, to some extent, be controlled by the size of the solid particulate material being used.

In one method according to the present invention, the particulate material is soluble in a first solvent and the body material, i.e., metals, polymers, or metals and polymers, is not soluble in the first solvent. The body material may be soluble in a second solvent, although that is not required. By forming the body with a material that is insoluble in the first solvent, the particulate material can be introduced into the body as it is being formed. After the body is formed (with the particulate material at least partially encapsulated therein), the body can be contacted with the first solvent to dissolve the particulate material, thereby forming the recesses and passageways in the body that are described above.

Although the particulate material is preferably at least partially encapsulated by the body, it will be understood that some of the particulate material will be completely encapsulated by the material forming the body. The portion of the particulate material that is completely encapsulated may remain within the body of the stent after the portion of the particulate material exposed to the first solvent has been removed. As a result, it is preferred that the solid particulate material be biocompatible.

Further, it will be understood that the portion of the solid particulate material that is only partially encapsulated by the body material will be partially exposed, where it can be acted on by the first solvent as described herein.

Although films for stent bodies according to the present invention can be manufactured separately from the support structure of the stent and attached to the support structure after formation, the preferred methods according to the present invention include forming the films directly on the support structure such that the support structure is at least partially, preferably completely, encapsulated by the film. By at least partially encapsulating the support structure in the films, the integrity of the resulting stent is improved. In addition, the support structure can comprise, e.g., a metal wire, that can provide improved structural characteristics as compared to stents formed completely of films.

The remainder of the detailed description will be based on the following exemplary embodiment.

A flexible, polymeric film is applied to spaced-apart metal elements such that it extends between the metal elements to form a 360 degree coverage of the body lumen along at least a portion of the length of the cylindrical stent.

Figure 2:
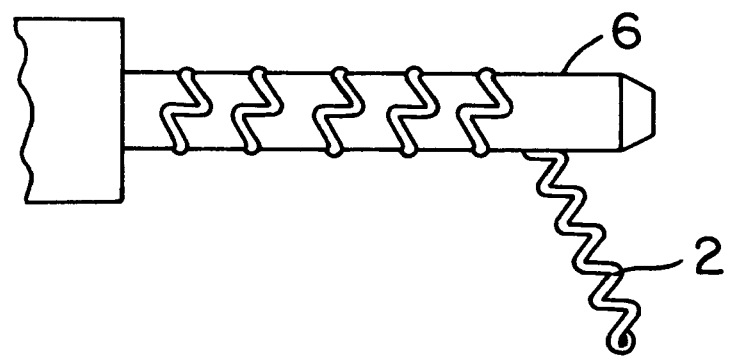
FIG. 2 is an elevational view of the wire of FIG. 1 being wound on a mandrel to produce a hollow cylinder.

A stent of suitable configuration is shown in FIGS. 1–2. A tantalum wire 2 (having a preferred diameter in the range of about 0.005 inch to 0.010 inch) is initially preformed into a two-dimensional zig-zag form, basically creating a flat expandable band 4. The zig-zag pattern can vary as to its shape and the tightness of the reversing bends. A convenient way of forming the band 4 is to run the wire through a set of co-acting gears. The flat expandable band is then wound in a helical direction on a mandrel 6 to form a hollow cylindrical shape. Application of the polymeric film takes place with the cylindrical stent wire applied to a cylindrical mandrel which is preferably sized to approximately the diameter of the fully expanded stent. For example, for a 3.0 mm expanded diameter stent, a 3.0 mm diameter Pyrex glass rod can serve as the mandrel. Optionally, the wires can be pretreated to promote adhesion between the film and the wires.

With the wire elements located around the mandrel (they may be either in contact with the mandrel surface or loosely wound around the mandrel as desired), a particulate material is applied to the mandrel and stent such that it is lightly adhered to the mandrel. The particulate material should be readily soluble in a solvent which will not also dissolve the polymer chosen for the film. For example, crystalline sodium bicarbonate is a water soluble material that can be used as the particulate material.

The particulate material can range from less than about 1 micrometer in diameter to about 1000 micrometers, preferably about 1 micrometer to about 100 micrometers, more preferably about 25 micrometers to about 60 micrometers. For uniformity of recesses on the blood-contacting surface of the stent, the sodium bicarbonate particles can be screened through successively finer mesh sieves. For example, the sodium bicarbonate can be successively screened through 100, 170, 270, 325, 400 and 500 mesh analytical grade stainless steel mesh sieves to produce a desired range of particle sizes. In particular, material that passed the 400 mesh sieve (38 microns in diameter) but did not pass the 500 mesh sieve (25 microns in diameter) were used to make test devices but other fractions could also be used. A nonaqueous liquid, preferably a solvent for the polymer film material, can be applied to the mandrel before applyingthe particulate material in order to retain more of the particulate material on the mandrel. For example, when a polyurethane is to be used for the film material, the solvent 1-methyl-2-pyrrolidinone (NMP) can be used to wet the surface of the mandrel before the application of particulate material. Preferably, the mandrel is completely dusted with the particulate in the portions of the mandrel to be coated with the polymer film. This can be accomplished by dipping the mandrel in NMP, allowing it to drain vertically for a few seconds and then dusting the sodium bicarbonate onto the mandrel while rotating it horizontally until no further bicarbonate particles adhere. Excess particulate material can be removed by gently tapping the mandrel.

Coating with polymer may proceed immediately following application of the particulate material. A polymer is provided in a dilute solution and is applied to the particle-coated stent and mandrel. The polymer chosen for the coating can be a biostable or a bioabsorbable material having a demonstrated low potential for foreign body response. A particularly useful material is an ether-free biostable polyurethane as disclosed in U.S. Pat. No. 4,883,854, which incorporated herein by reference in its entirety. The polyurethane can be dissolved in NMP to make a 10% solution. Gel particles and particulate impurities can be removed from the solution by use of a clinical centrifuge.

Figure 3:
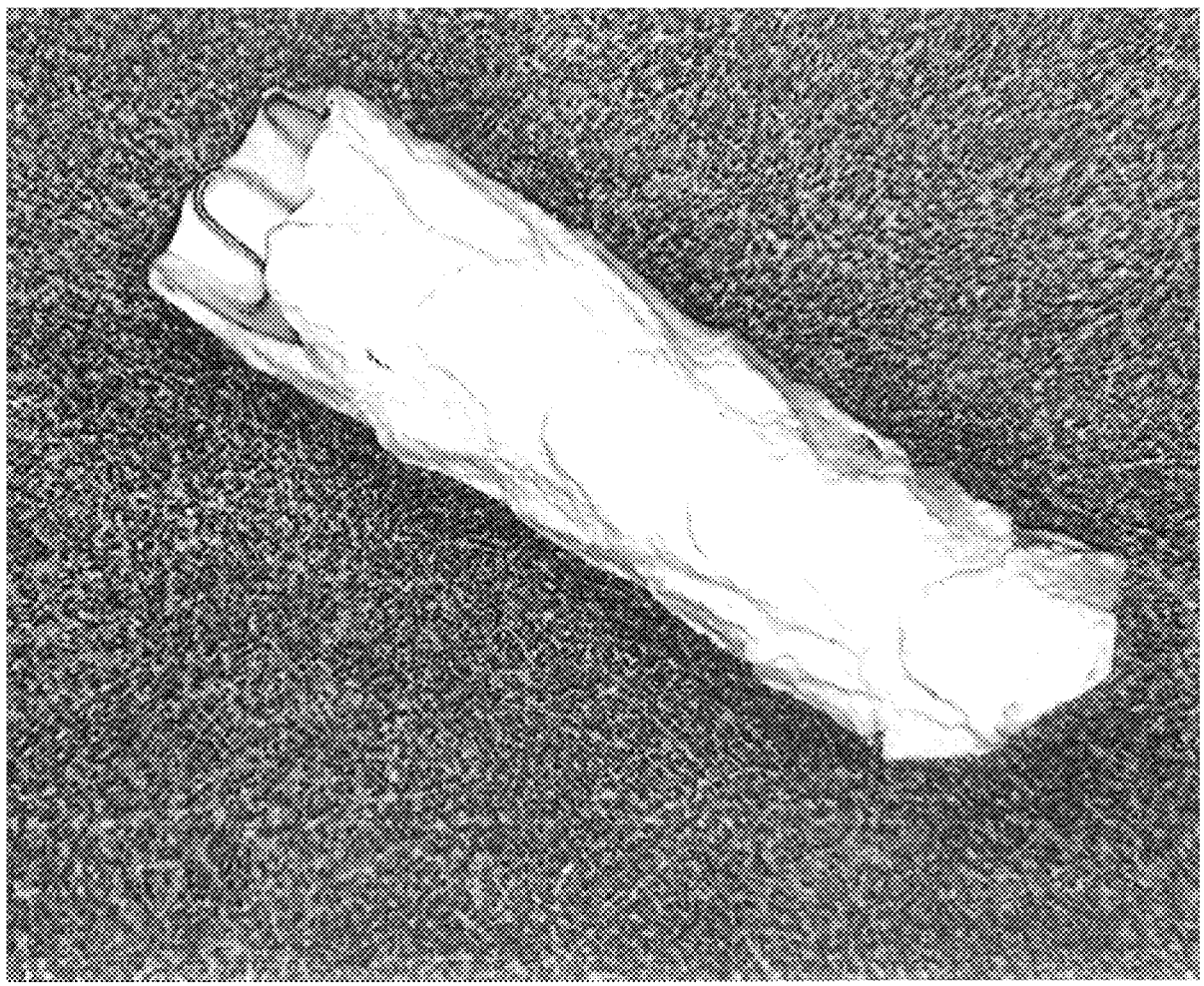
FIG. 3 is a photograph of a completed stent according to the present invention.
Figure 4:
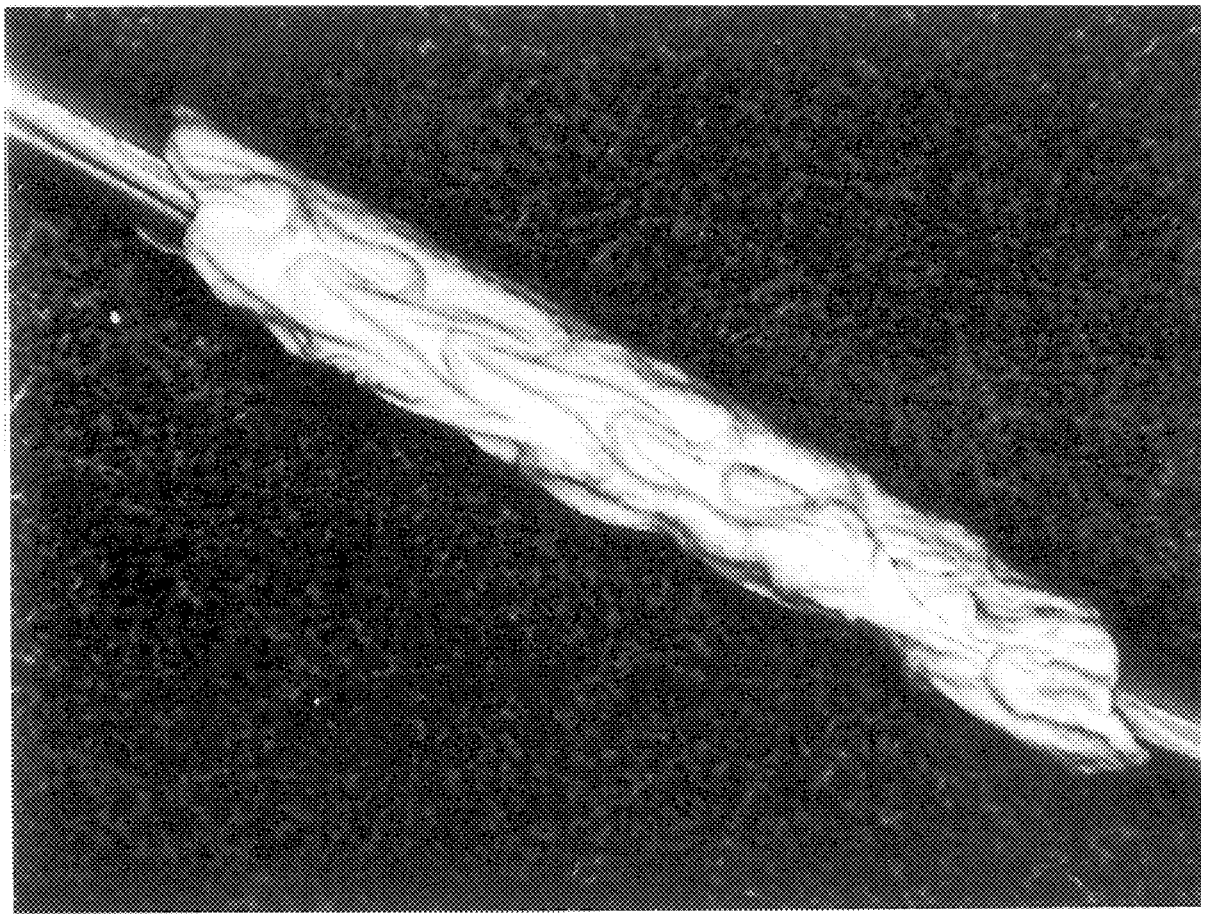
FIG. 4 is a photograph of the stent of FIG. 3 compressed onto a balloon delivery catheter.
Figure 5:
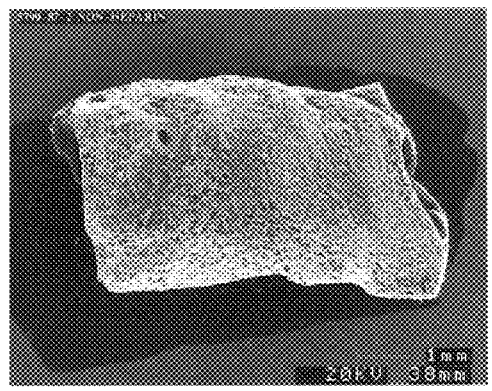
FIG. 5 is a photograph of a polymeric film without a heparin coating.
Figure 6:
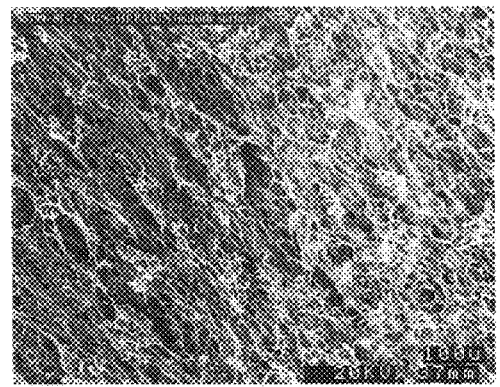
FIG. 6 is a photograph of the outside surface of the polymeric film of FIG. 5 at higher magnification.
Figure 7:
FIG. 7 is a photograph of the inside surface of the polymeric film of FIG. 5 at higher magnification.
Figure 8:
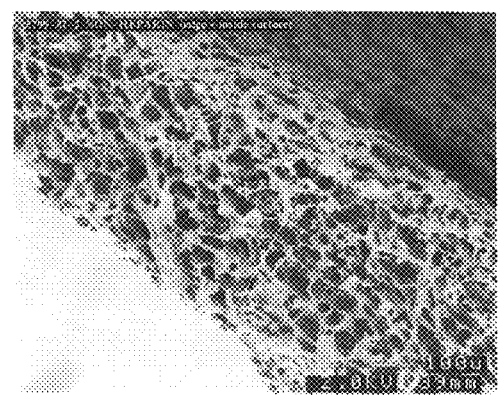
FIG. 8 is a photograph of an edge surface of the polymeric film of FIG. 5 at higher magnification.
Figure 9:
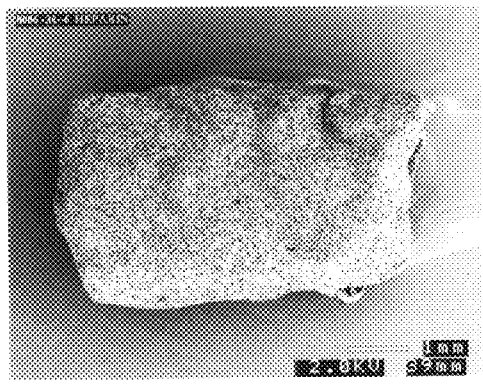
FIG. 9 is a photograph of a polymeric film with a heparin coating.
Figure 10:
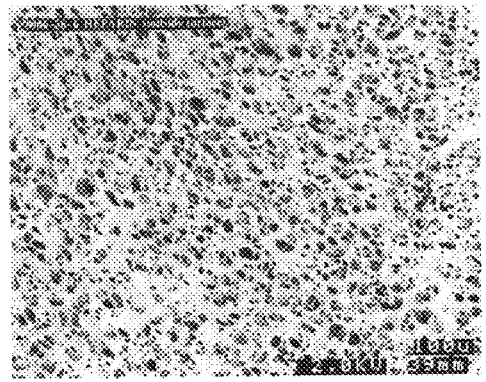
FIG. 10 is a photograph of the outside surface of the polymeric film of FIG. 9 at higher magnification.
Figure 11:
FIG. 11 is a photograph of the inside surface of the polymeric film of FIG. 9 at higher magnification.
Figure 12:
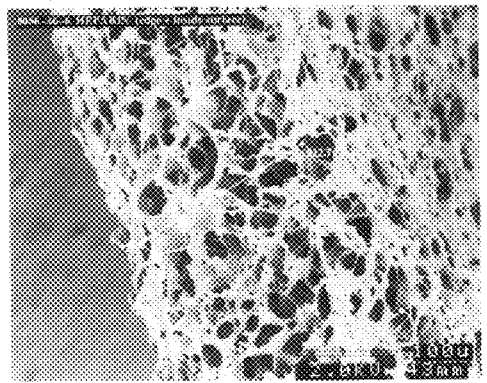
FIG. 12 is a photograph of an edge surface of the polymeric film of FIG. 9 at higher magnification.

The polymer solution can be applied by dipping the mandrel into the solution and letting the solvent evaporate. With the solution of polyurethane and NMP set forth above, a single dip in the solution can provide a film of adequate thickness. To assist in the formation of communicating passageways through the polymer between the blood-contacting surface and the lumen-contacting surface, additional sodium bicarbonate particles are preferably dusted onto the polymer solution immediately after the dipping operation and before the polymer solution has dried. Excess particulate material can be removed by gently tapping the mandrel. To precipitate and consolidate the polyurethane film on the stent, it can be dipped briefly (about 5 minutes) in water and then rolled gently against a wetted surface, such as a wet paper towel. The stent assembly can then placed into one or more water baths over an extended period (e.g., 8 hours) to dissolve and remove the sodium bicarbonate. After drying in air at temperatures from about 20 degrees Centigrade to about 50 degrees Centigrade, the film then may be trimmed to match the contour of the wire. The device so made is shown in FIG. 3 in its expanded form and in FIG. 4 as it is compressed onto a balloon catheter for delivery into the blood vessel. FIGS. 5–8 depict the surface characteristics of the film at various portions of the surface.

The surfaces having recesses so provided are then also provided with a grafted antithrombogenic or thrombolytic surface which does not obstruct the recesses and passageways described above. The antithrombotic or thrombolytic surface is preferably provided by covalently binding a bioeffective antithrombotic or thrombolytic agent onto the blood-contacting surface. The antithrombotic or thrombolytic agent can usually also be provided conveniently onto the lumen-contacting surface of the device although such a coating is not believed to be as important as its application to the blood-contacting surface.

The preferred antithrombotic is heparin which has been immobilized onto the surface of the device in a manner which preserves the biofunctionality of the heparin molecule. By heparin, we mean a heterogeneous group of straight-chain anionic mucopolysaccharides having anticoagulant properties. The heparin used herein can be a preparation obtained from tissues in a manner conventional for the preparation of heparin as an anticoagulant. The heparin preparation can be obtained from a variety of mammalian tissues, including, if desired, human tissue. Generally, porcine or bovine sources are used with a preferred tissue for heparin starting material being porcine intestinal mucosa. Heparin preparations prepared from this tissue source are commercially available.

The blood-contacting surface of the device is prepared for heparin grafting by providing it with immobilized amine groups which are capable of bonding to aldehyde groups on the heparin molecule. Such amine groups can be provided by methods known to those skilled in the art. For example, amine-functional spacer molecules have been used to immobilize a biomolecule and/or biomolecules. The spacer insures that the active site of the biomolecule is held outward away from the support so as to contact the body fluid efficiently. The spacers are derived from organic molecules having two reactive functional groups, or more, generally situated at opposing ends of the molecule. Such groups serve as attachment vehicles capable of coupling the spacer to the solid surface and to the biomolecule. For example, in U.S. Pat. No. 5,132,108 to Narayanan et al., a copolymer surface was subjected to radiofrequency plasma treatment by subjecting it to a radiofrequency electric field in the presence of a water vapor plasma medium. An aqueous solution of polyethyleneimine (PEI) and 1-(3-dimethylpropyl)-3-carbodiimide (EDC) coupling agent was applied to the radiofrequency plasma discharge modified polyurethane surface. An aqueous solution of heparin and EDC was then applied to the PEI-treated surface in order to provide a polymeric surface having an anti-thrombogenic agent secured to its surface. According to U.S. Pat. No. 4,565,740 to Golander et al. or U.S. Pat. No. 5,049,403 to Larm et al, a complex of a polymeric cationic surfactant (e.g. a polyalkyleneimine) and a difunctional aldehyde (e.g. glutaraldehyde or crotonaldehyde) is adsorbed onto a substrate material. Multiple coatings, including intermediate layers of anionic material are then applied to obtain an effective coating. Other improvements in biocompatibility of biomaterials are disclosed in the use of multilayer coatings in U.S. Pat. Nos. 5,229,172; 5,308,641 and 5,350,800 which are incorporated herein by reference. For example, in U.S. Pat. No. 5,229,172, a method is disclosed for modifying the surface characteristics of a polymeric material by providing a base layer of grafted acrylamide on the polymeric surface which can be used to attach various spacers and biomolecules. Or, in U.S. Pat. No. 5,308,641, is disclosed an improved spacer material which includes a polyalkyeneimine covalently attached to an aminated substrate and crosslinked with a crosslinking agent which is difunctional in aldehyde groups. Or, in U.S. Pat. No. 5,350,800, a method is disclosed for attaching a biomolecule having carboxyl groups to an aminated solid surface by a carbodiimide and then selectively restoring the bio-functionality of the carboxyl groups. On metal surfaces, the binding of the base layer of such multi-layer coatings can be a problem since there is no organic structure to provide covalent bonds between the metal or glass substrate and the grafted base layer. Others have addressed the problem of binding to metals by applying aminosilanes to adhere to the surface and then attaching the biomolecule to the aminosilane through the amine functionality of the aminosilane. This can be seen in U.S. Pat. No. 5,355,433 issued to Rowland et al in which an aminosilane is used to adhere a heparin molecule to an oxidized tantalum surface. Aminosilanes are also disclosed for attachment of a heparin molecule to metal surfaces in U.S. Pat. No. 4,118,485 issued to Eriksson et al. Any of these methods could be used in the present invention so long as the coating is applied in a manner which prevents the recesses in the polymer surface from being occluded.

Preferably, the immobilized amine functionality is provided in a manner similar to that disclosed in U.S. Pat. No. 5,308,641 in which a polyalkyeneimine is covalently attached to a substrate. By polyalkyleneimine, we mean to include the water soluble, hydrophilic, polyamines evolving from aziridine and azetidine monomers such as 1-unsubstituted imines, 1-substituted basic imines, activated imines (1-acyl substituted imines), isomeric oxazolines/ oxazines and the like. The polyalkyleneimines employed in the present invention are preferably highly branched, thereby possessing primary, secondary, and tertiary amine groups. Thus, ethyleneimine polymerized by classical cationic chain-growth polymerization, either alone or with other monomers suitable for copolymerization with ethyleneimine, could be used in the present invention. The preferred molecular weight of such a polyethyleneimine could range from about 60,000 to about 1,000,000.

The polyethyleneimine can be attached to a polymer which is grafted to the surface of the film material. The grafting reaction preferably includes grafting of acrylamide and/or acrylic acid monomers to the polymer surface. The resulting surface then has a large number of covalently grafted carboxyl groups which may be used to attach the polyethyleneimine to the device surface. Preferably, the grafting solution is an aqueous mixture of acrylamide, acrylic acid and ceric ion. Preferably, The grafting reaction may be carried out at temperatures between about 18° C. and 25° C. The pH of a grafting solution with ceric ammonium nitrate is typically about 1.4.

The amount of cerium ion utilized in the practice of the process of the present invention can be varied over fairly wide limits. For example, one may utilize from about 0.0001 to 0.002 mole of ceric ion per mole of polymerizable monomer. Preferably one would use between 0.0002 to 0.0006 mole of ceric ion per mole of polymerizable monomer. Ceric ion is preferably introduced into the reaction mixture in the form of a ceric salt. Among the cerium salts adapted for use in the present invention are ceric nitrate, ceric sulfate, ceric ammonium nitrate, ceric ammonium sulfate, ceric ammonium pyrophosphate, ceric iodate, ceric salts of organic acids, such as cerium naphthenate and cerium linoleate and the like. These compounds may be employed singly or in combination with one another.

In general, the time required to achieve a desired degree of polymerization may be determined empirically. Thus, for example, acrylamide and/or acrylic acid may be grafted at different time intervals and the extent of grafting determined by staining of functional groups introduced in the graft by chemical modification. The length of the polymeric chain and graft density may be varied by varying the acrylamide and/or acrylic acid concentration, ceric ion concentration and temperature. On some polymer materials it may be desirable to irradiate the material to provide additional functional groups to improve the grafting process. It may also be desirable to include a polymerization inhibitor such as copper nitrate in the reaction mixture in order to control the grafting reaction. An important aspect of the grafted coating for the present invention is to maintain a very thin graft layer so as to prevent occlusion of the recesses on the film. This can be accomplished by carefully removing any loosely bound graft polymer from the film surface. With the polyacrylamide/polyacrylic acid graft polymer described above, this can be accomplished by water washing the surface with a stream of water.

Attachment of the polyethyleneimine to the grafted surface can be accomplished by the use of a water soluble carbodiimide of the structure $R_1N=C=NR_2$ where $R_1$ can be an alkyl or cycloalkyl group and $R_2$ can be an alkylamine or cycloalkylamine group such as 1-ethyl-3-(3-dimethylaminopropyl)carbodiimide hydrochloride, or 1-cyclohexyl-3-(2-morpholinoethyl)carbodiimide. This reaction is preferably undertaken in a cold solution (0–4° C.) at a pH of about 5 although a room temperature reaction is also acceptable. The grafted can be pretreated with carbodiimide and then be brought into contact with the polyethyleneimine where the carbodiimide, polyamine and grafted surface can react concomitantly. In the process, the carbodiimide reacts with the carboxyl groups on the grafted surface forming labile O-acylisourea esters (1), susceptible to nucleophilic substitution. Reaction with an amine leads to the formation of a suitable amide bond (2), resulting in effective immobilization of the polyethyleneimine.

Attachment of the heparin molecules to the polyethyleneimine requires treatment of the heparin to produce reactive aldehyde molecules on the heparin which can react with primary amine groups on the crosslinked polyethyleneimine.

Controlled oxidation of the heparin molecules to provide a limited number of reactive aldehyde groups on the heparin molecule is accomplished by treatment with such compounds as nitrous acid or sodium periodate. Preferably, the heparin is treated by controlled oxidation with periodate. Any water soluble periodate can be used but preferably the periodate is an alkali metal periodate such as sodium periodate. The amount of periodate required is that sufficient to react with no more than two of the sugar units in the heparin molecule. By sugar, we mean the basic disaccharide residues constituting the structure of the glycosaminoglycan. If the periodate used is sodium periodate and the heparin used is a commercially available injectable form of heparin (i.e. its sodium salt with activity of 160 u/mg), the weight ratio of heparin to periodate should be about 30:1 or greater in order to react with no more than two of the sugar units in the heparin molecule. It will be appreciated by those skilled in the art that the amount of periodate required for other periodate compounds and other forms of heparin can be determined by conventional calculation and empirical tests.

The reaction between heparin and periodate takes place in an aqueous buffer solution. Generally, buffers having a pH in a neutral to slightly acidic range of about 4.5 to 8 can be used with lower pH (e.g. an acetate buffer at pH=4.5) being preferred if a rapid reaction is desired while a more neutral pH (e.g. a phosphate buffer at pH=6.88) is preferred for a slower reaction with a longer storage life. With the acetate buffer at a pH of 4.5, the reaction should proceed for about 3 hours while with a phosphate buffer at a pH of 6.88, the reaction should proceed for about 16 hours. If desired, the reacted solution may then be stored prior to use at about 5° C. The storage stability of the reacted mixture at a neutral pH can extend for 2 to 14 days. The reactive mixture may then be applied to the immobilized amine groups on the surface. Preferably, the reaction mixture is first diluted and the pH adjusted in order to bring the pH of the mixture to a pH which is favorable for the coupling reaction. For example, the reaction mixture can be diluted in an acetate buffer solution (pH=4.5). A mild reducing agent such as sodium cyanoborohydride is added to the diluted mixture to effect the reduction of the bonds formed between the reactive aldehyde groups on the oxidized heparin and the amine-functional groups immobilized on the surface to be treated. The surface to be treated is then immersed in the diluted mixture and incubated at a sufficient temperature and time to complete the reaction. For example, the reaction could be competed in about 1–3 hours at 50° C. Alternatively, the reaction could be completed at room temperature over a longer period of time. A surface made according to this method is shown in FIGS. 9–12.

Figure 13:
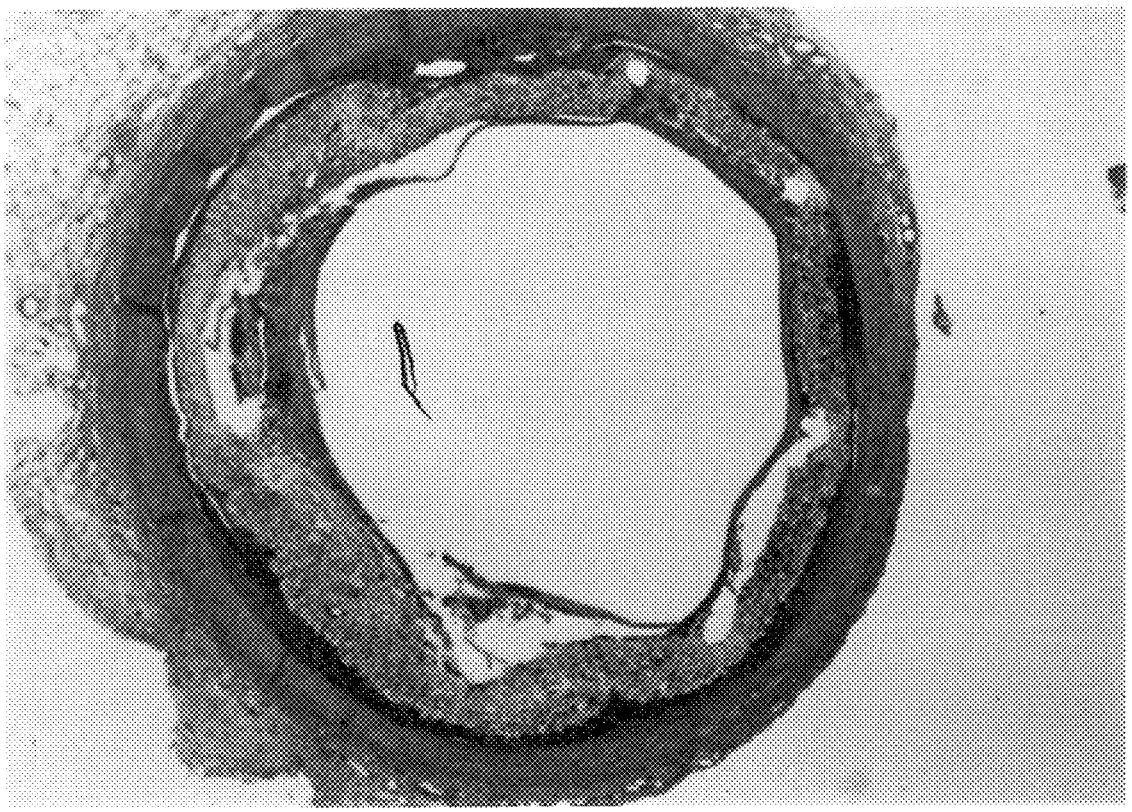
FIG. 13 is a photograph of a cross-section of an uninjured artery and implanted stent according to the present invention.
Figure 14:
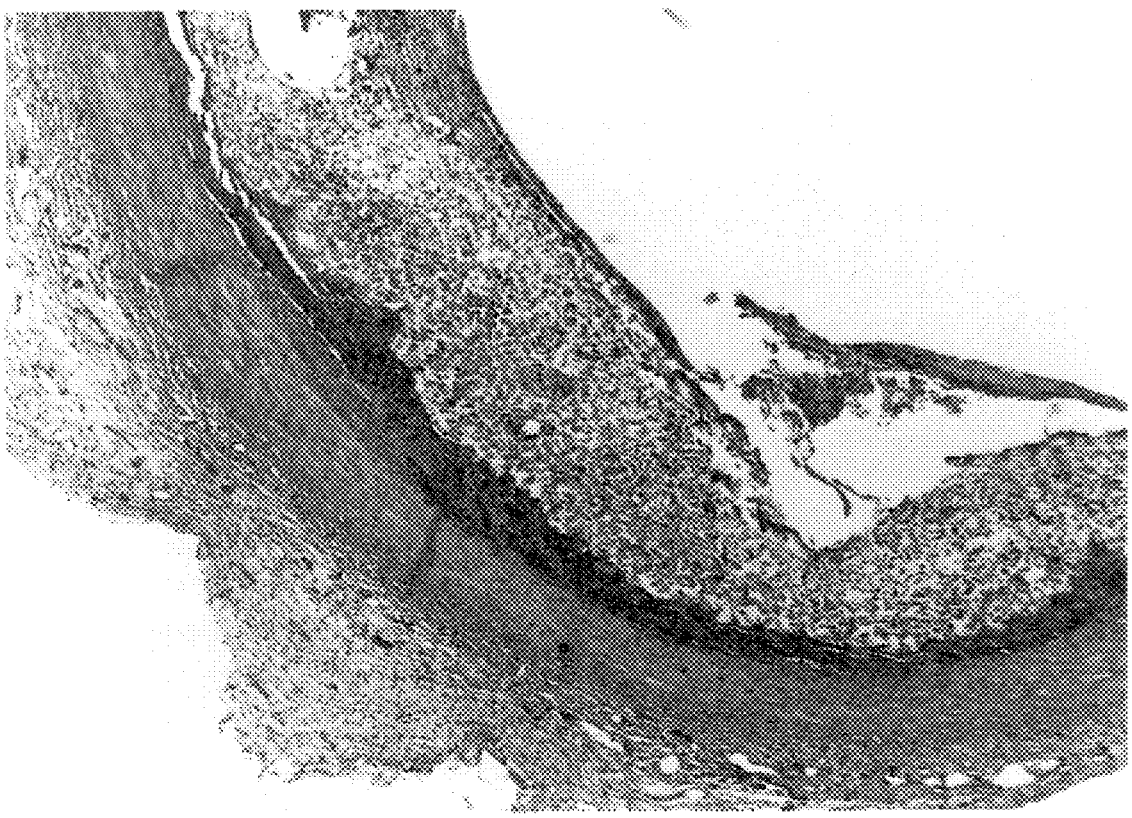
FIG. 14 is a magnification of a portion of the photograph of FIG. 13.
Figure 15:
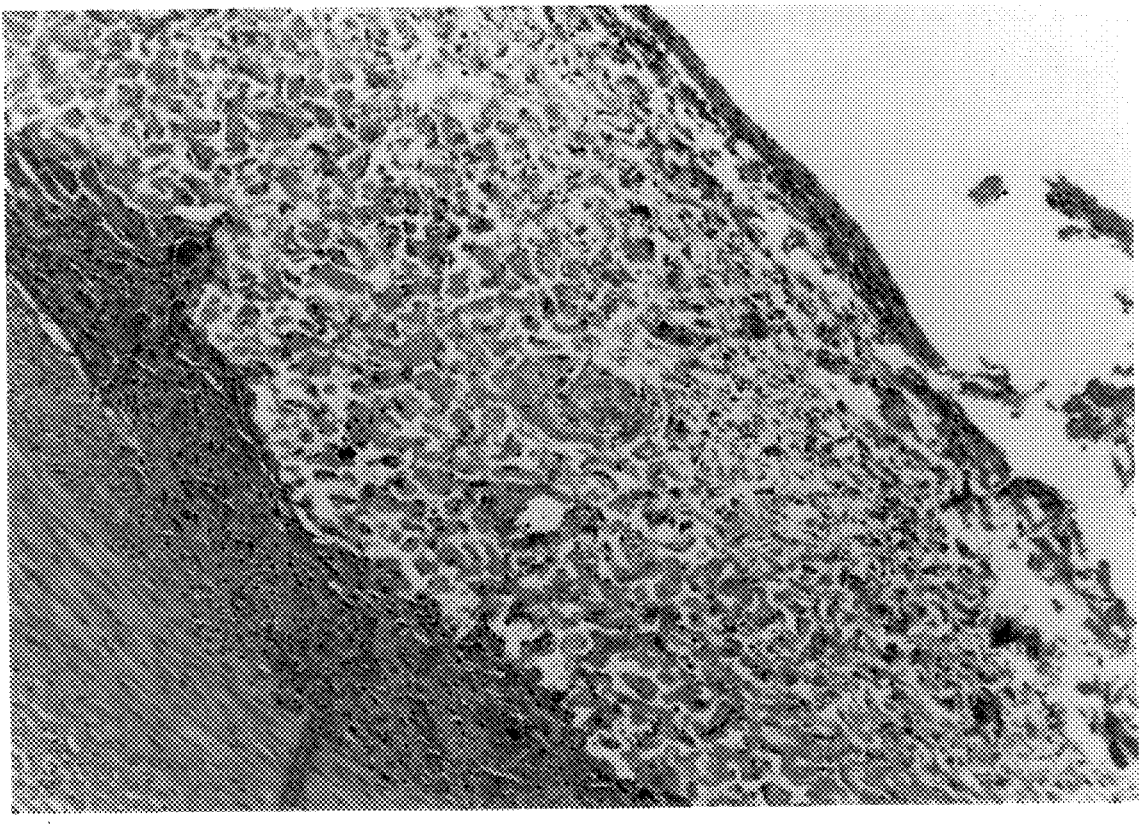
FIG. 15 is a magnification of a portion of the photograph of FIG. 13.
Figure 16:
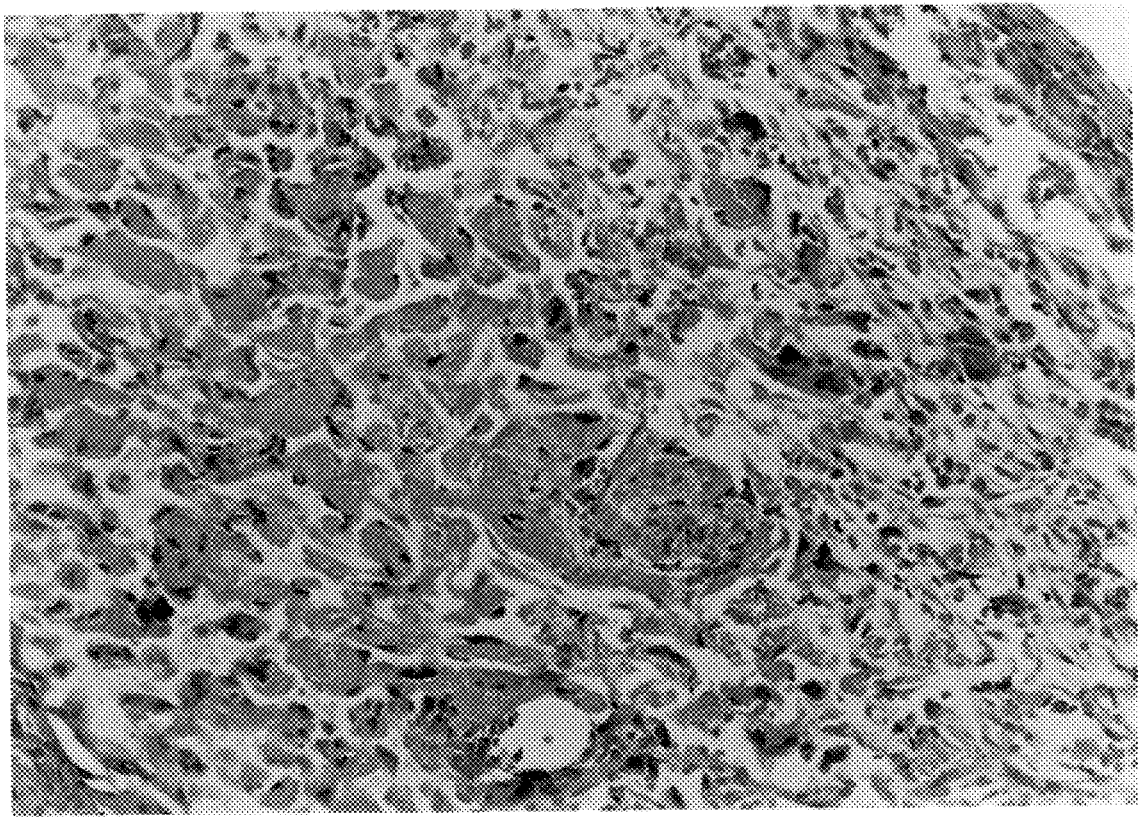
FIG. 16 is a magnification of a portion of the photograph of FIG. 13.
Figure 17:
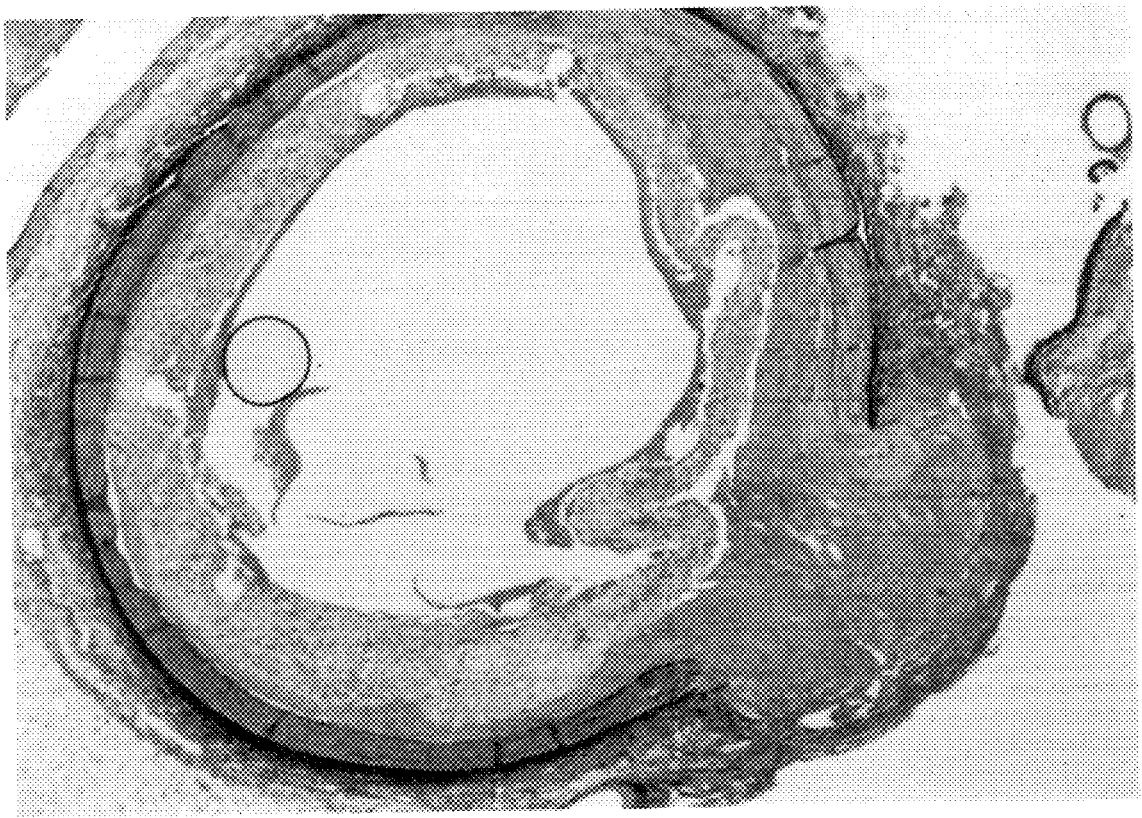
FIG. 17 is a photograph of a cross-section of an injured artery and implanted stent according to the present invention.
Figure 18:
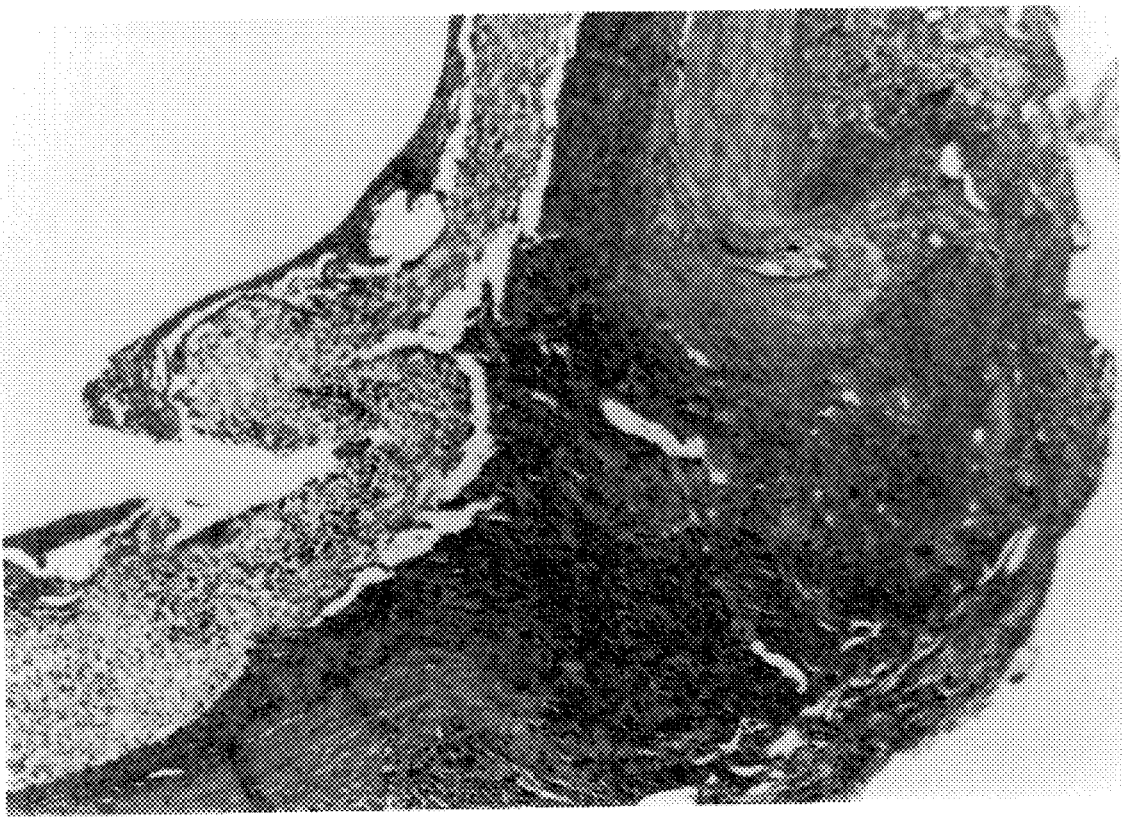
FIG. 18 is a magnification of a portion of the photograph of FIG. 13.
Figure 19:
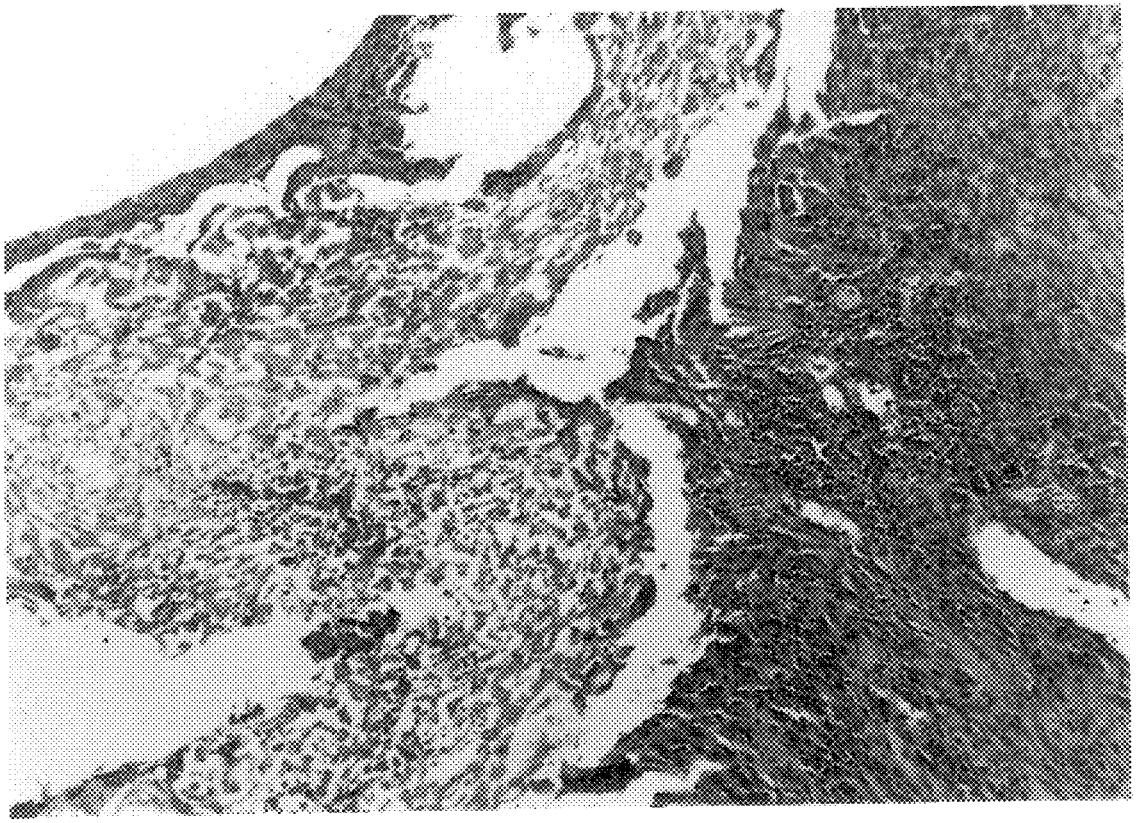
FIG. 19 is a magnification of a portion of the photograph of FIG. 13.
Figure 20:
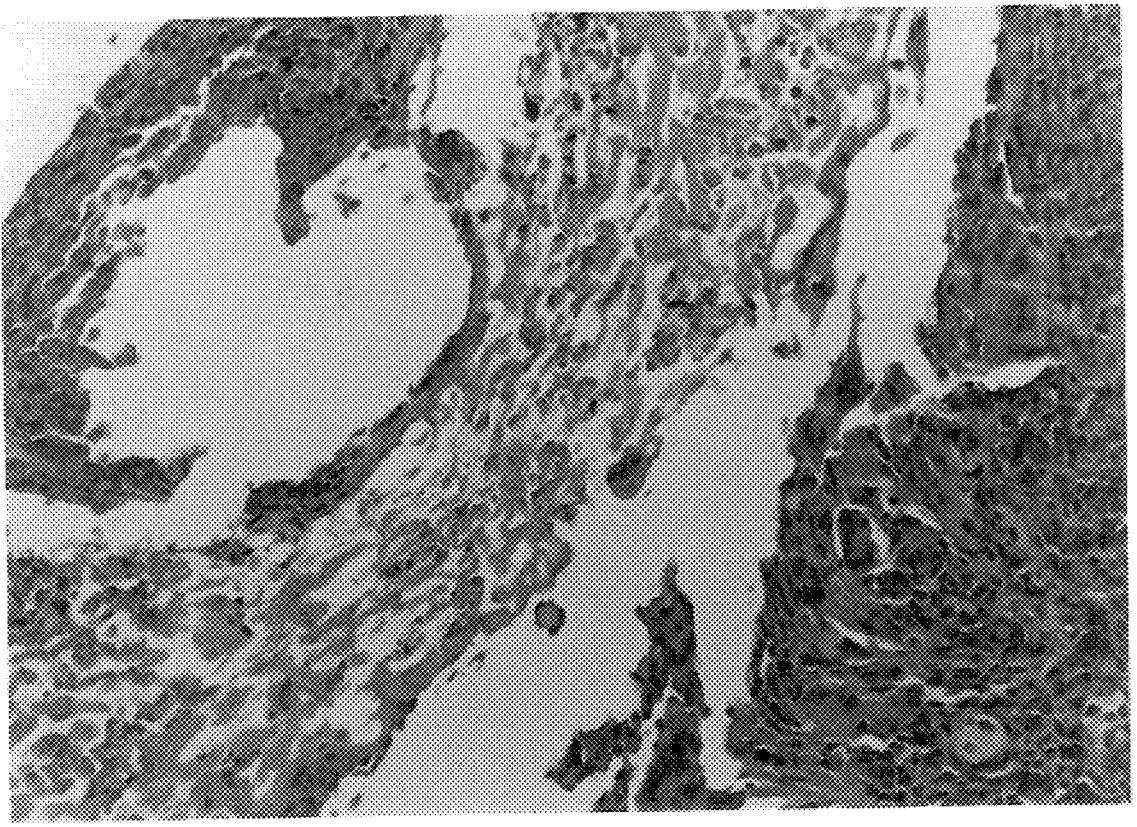
FIG. 20 is a magnification of a portion of the photograph of FIG. 13.

Delivery of the stent described above is accomplished on a balloon catheter by methods which are well known in the art. The stent is placed on a catheter and delivered to the remote portion of the body lumen to be treated where it is expanded into contact with the inner luminal surface. Controlled radial expansion of the stent is accomplished by the force generated in inflating the balloon on which it is mounted for delivery. The radial expansion is achieved by controlled deformation and tension applied to the sinusoidal pattern of the preformed wire band with minimal resistance from the film. The catheter is then withdrawn from the body lumen. The low memory metal used for the fabrication of the wire formed stent and flexibility of the film assures that the radially expanded stent stays expanded as a permanent implant in the vessel thus fulfilling its primary intent and function to provide support in a body lumen such as a blood vessel for any flaps or dissections in the lumen wall. Animal testing of the device in a porcine model included successful application of the invention in both uninjured and injured arteries. FIGS. 13–16 show the results of a 28 day implant in an uninjured artery. FIGS. 13 and 14 show the development of a very thin neointima over the stent and FIGS. 15 and 16 show the porosity of the film of the stent and the migration of cells into the passageways of the film. FIGS. 17–20 show the results of a 28 day implant in an injured artery. FIGS. 17 and 18 show that the injury has been contained with only a thin neointima produced at the site of the injury. FIGS. 19 and 20 show the porosity of the film and the migration of cells into the passageways of the film.

Further, since the stent of the present invention has a relatively large surface area in contact with the body lumen, the stent may also incorporate other therapeutic substances in or on the film such as those disclosed in published international patent application WO 91/12779 "Intraluminal Drug Eluting Prosthesis", which is incorporated herein by reference. The stent can then be used to administer such therapeutic substances to the vessel and to the bloodstream for the prevention of thrombosis or prevention of restenosis in the vessel.

It will be appreciated by those skilled in the art that a film material with recesses can be applied to the windings of the stent by other means than those described above. For example, a preformed film for the desired thickness can be applied to the stent windings by wrapping a sheath of the film material around the stent windings or by winding the film around the windings. In the case of a relatively inelastic film material, the film can be provided with folds or pleats when attached to the stent in order to provide the necessary flexibility and expandability. Mechanical or adhesive attachment methods can be used to attach the film to the windings.

It will be appreciated by those skilled in the art that while the invention has been described above in connection with particular embodiments the invention is not necessarily so limited and that numerous other embodiments, uses, modifications and departures from the embodiments, and uses may be made without departing from the inventive concepts.

What is claimed is:

1. A method of manufacturing an intraluminal stent having a body, the body having an outer surface and an inner surface, the method comprising steps of:

forming the body with a film-forming material;

providing solid particulate material at least partially encapsulated in the body, the particulate material being soluble in a first solvent;

dissolving the particulate material with the first solvent, wherein a plurality of recesses are formed in the inner and outer surfaces of the body, and further wherein at least some of the plurality of recesses in the inner surface open into at least some of the plurality of recesses in the outer surface to form a plurality of passageways between the inner and outer surfaces of the body; and coating at least the inner surface of the body with an antithrombotic substance, wherein at least some of the plurality of passageways remain open after the antithrombotic substance is coated on the body.

2. A method according to claim 1, wherein the body comprises a substantially cylindrical film formed on a support structure comprising spaced apart elements.

3. A method according to claim 2, wherein the film has a thickness of about 25 micrometers to about 400 micrometers.

4. A method according to claim 3, wherein the plurality of recesses have a nominal size of about 1 micrometer to about 100 micrometers.

5. A method of manufacturing an intraluminal stent having a body, the body having an outer surface and an inner surface, the method comprising steps of:

coating at least a portion of a mandrel with solid particulate material, the particulate material being soluble in a first solvent;

forming the body on the particulate-coated mandrel with a film-forming material that is substantially insoluble in the first solvent, the body at least partially encapsulating the particulate material; and dissolving the particulate material with the first solvent, wherein a plurality of recesses are formed in the body.

6. A method according to claim 5, wherein the plurality of recesses are formed in the inner surface and outer surface of the body.

7. A method according to claim 6, wherein at least some of the plurality of recesses in the inner surface open into at least some of the plurality of recesses in the outer surface to form a plurality of passageways between the inner and outer surfaces of the body.

8. A method according to claim 7, further comprising a step of coating at least the inner surface of the body with an antithrombotic substance, wherein at least some of the plurality of passageways remain open after the antithrombotic substance is coated on the body.

9. A method according to claim 8, wherein the step of forming the body further comprises wrapping a wire around the mandrel before forming the body on the mandrel with the film-forming material, wherein the wire is at least partially encapsulated within the body, and further wherein the body is a film having a thickness of about 25 micrometers to about 400 micrometers.

10. A method according to claim 9, wherein the plurality of recesses have a nominal size of about 1 micrometer to about 100 micrometers.

11. A method according to claim 10, wherein the film-forming material comprises a polymer.

12. A method according to claim 11, wherein the solid particulate material has a nominal diameter of about 25 micrometers to about 60 micrometers.

13. An intraluminal stent for supporting a portion of a vessel comprising:
   a support structure comprising spaced apart elements;
   a body having a generally cylindrical shape, the body comprising a film at least partially encapsulating the spaced apart elements, the film having a thickness of about 25 micrometers to about 400 micrometers as measured between an outer surface and an inner surface of the film;
   a plurality of recesses in the inner and outer surfaces of the body, at least some of the plurality of recesses in the inner surface opening into at least some of the plurality of recesses in the outer surface to form a plurality of passageways between the inner and outer surfaces of the body; wherein the plurality of recesses have a nominal size of about 1 micrometer to about 100 micrometers; and
   an antithrombotic substance on at least the inner surface of the body, wherein at least some of the plurality of passageways remain open.

14. A stent according to claim 13, further comprising a solid particulate material encapsulated within the film, the solid particulate material being soluble in a first solvent in which the film is substantially insoluble.

15. A stent according to claim 14, wherein the solid particulate material has a nominal diameter of about 25 micrometers to about 60 micrometers.

16. A method of manufacturing an intraluminal stent having a body, the body having an outer surface and an inner surface, the method comprising steps of:
   forming the body with a film-forming material;
   providing solid particulate material at least partially encapsulated in the body, the particulate material being soluble in a first solvent;
   dissolving the particulate material with the first solvent, wherein a plurality of open recesses are formed in the body; and
   coating the body with an antithrombotic substance such that at least some of the plurality of recesses remain open.

17. A method according to claim 16, wherein the plurality of recesses are formed in the inner surface and outer surface of the body.

18. A method according to claim 16, wherein at least some of the plurality of recesses in the inner surface open into at least some of the plurality of recesses in the outer surface to form a plurality of passageways between the inner and outer surfaces of the body.

19. A method according to claim 16, wherein the body is a film formed on a support structure comprising spaced apart elements.

20. A method according to claim 19, wherein the film has a thickness of about 25 micrometers to about 400 micrometers.

21. A method according to claim 20, wherein the plurality of recesses have a nominal size of about 1 micrometer to about 100 micrometers.

22. A method of manufacturing an intraluminal stent having a body, the body having an outer surface and an inner surface, the method comprising steps of:
   forming a cylindrical body with a plurality of recesses in the inner surface and outer surface of the body wherein at least some of the plurality of recesses in the inner surface open into at least some of the plurality of recesses in the outer surface to form a plurality of passageways between the inner and outer surfaces of the body; and
   coating at least the inner surface of the body with an antithrombotic substance, wherein at least some of the plurality of passageways remain open after the antithrombotic substance is coated on the body.

23. A method according to claim 22, wherein the step of forming the body further comprises encapsulating a wire within the film-forming material.

24. A method according to claim 22, wherein the plurality of recesses are formed at a nominal size of about 1 micrometer to about 100 micrometers.

* * * * *